United States Patent [19]

Harris

[11] Patent Number: 5,567,870

[45] Date of Patent: Oct. 22, 1996

[54] BALL TESTER

[76] Inventor: William P. Harris, 112 Marble Canyon Dr., Folsom, Calif. 95630

[21] Appl. No.: 446,110

[22] Filed: May 19, 1995

[51] Int. Cl.⁶ ..................................................... G01N 3/48
[52] U.S. Cl. ..................... 73/81; 73/860; 73/85
[58] Field of Search ............................ 73/78, 81, 12.02, 73/82

[56] References Cited

U.S. PATENT DOCUMENTS

| | | | |
|---|---|---|---|
| 3,138,951 | 6/1964 | Scott | 73/81 |
| 3,696,662 | 10/1972 | Foltz et al. | 73/81 |
| 4,114,350 | 9/1978 | Snyder | 73/78 |
| 4,116,047 | 9/1978 | Hejkal | 73/81 |
| 4,136,554 | 1/1979 | Larson . | |
| 5,222,391 | 6/1993 | Reenstra . | |
| 5,291,774 | 3/1994 | Putnam, Jr. . | |

FOREIGN PATENT DOCUMENTS 7601334  12/1977  Netherlands .

Primary Examiner—Richard Chilcot
Assistant Examiner—Max H. Noori
Attorney, Agent, or Firm—Watson Cole Stevens Davis, P.L.L.C.

[57] ABSTRACT

A pair of arms are pivotally connected with each arm including a hand grip portion and a ball clamping portion. The clamping portions carry ball support members which support and center a ball within the tester. A gauge is mounted on one of the clamping portions and has a plunger which extends through one of the ball support members for engaging the outer surface of a ball. Movement of the clamping portions is limited by engagement of the end surfaces of the clamping portions. A torsion spring normally urges the hand grip portions away from one another. In one embodiment, the spring urges the clamping portions toward one another, and in another embodiment, the spring urges the clamping portions away from one another.

5 Claims, 2 Drawing Sheets

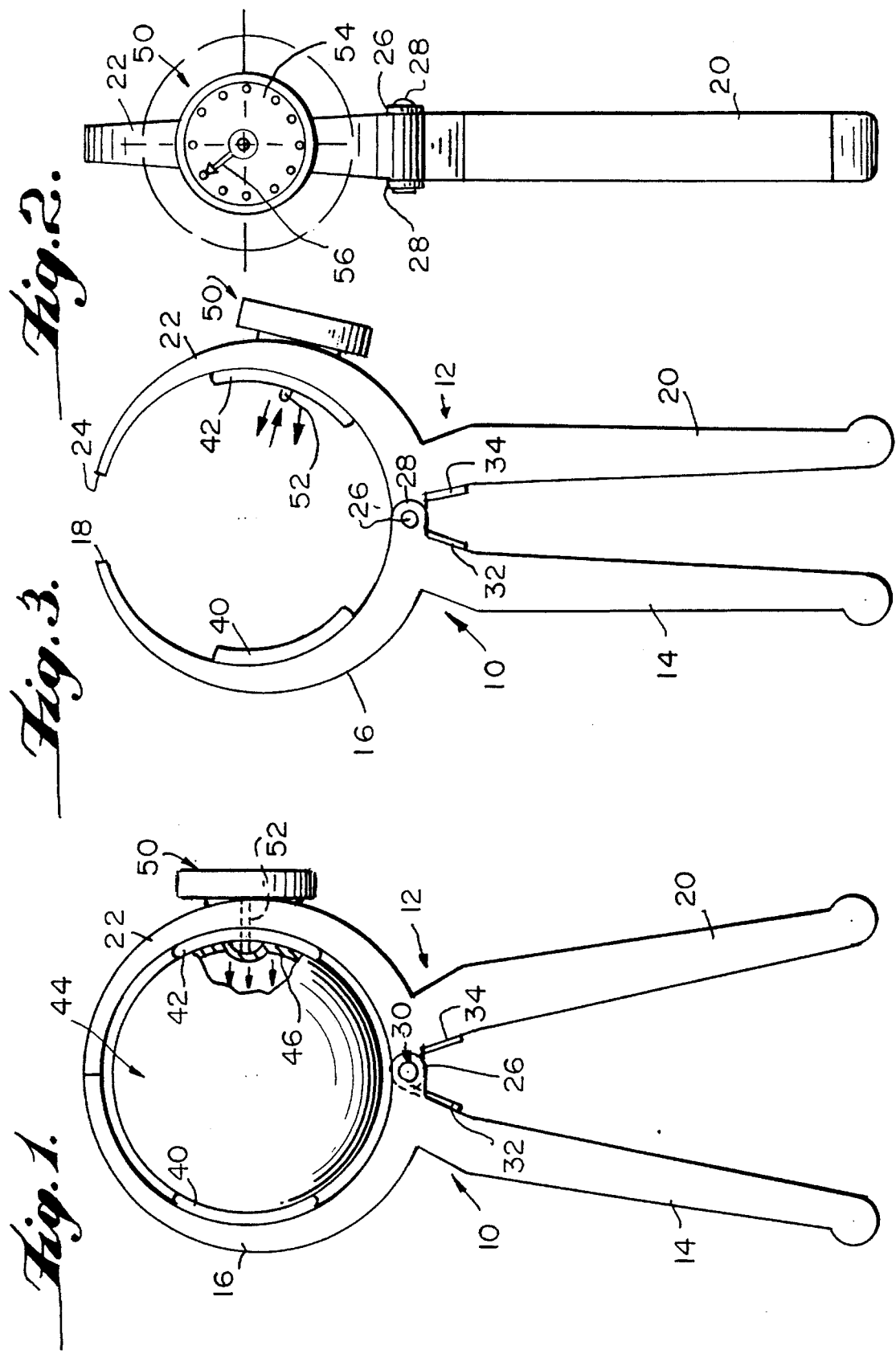

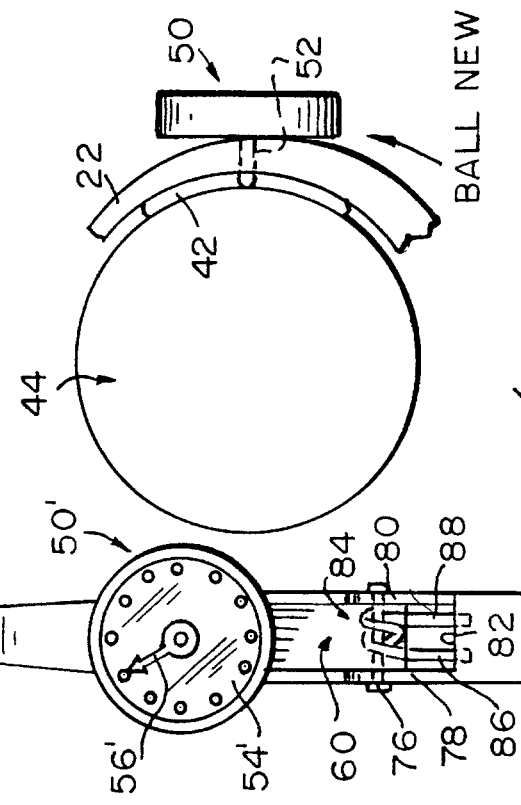
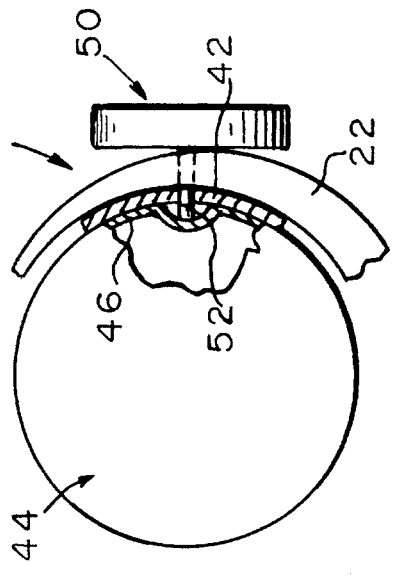
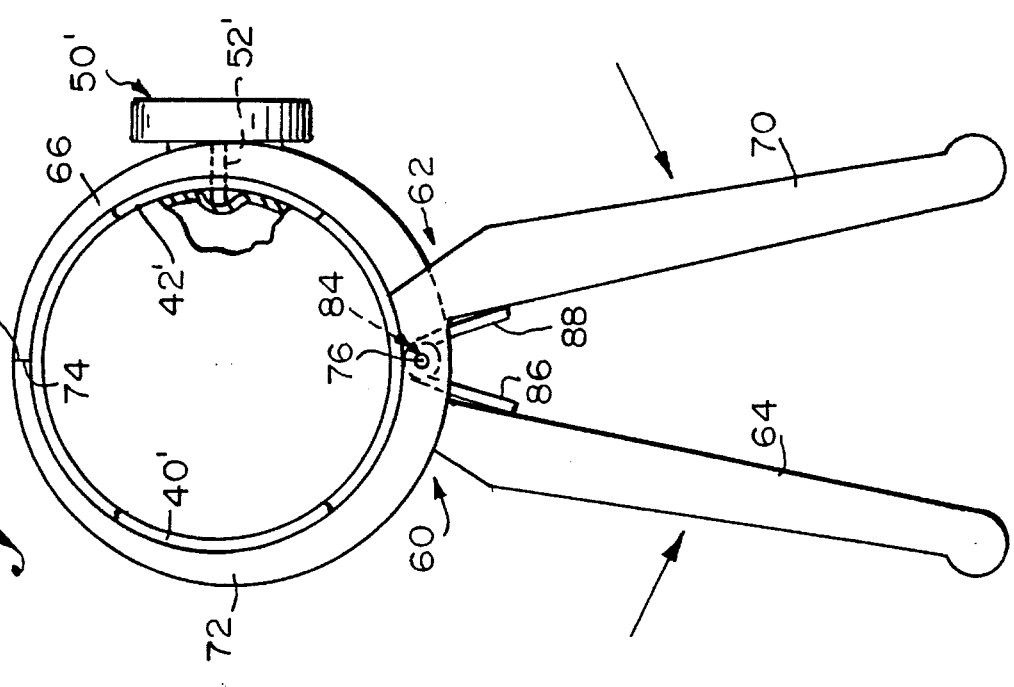

BALL TESTER

BACKGROUND OF THE INVENTION

The invention relates to a ball tester which is adapted to measure the interior inflation pressure and playing condition of balls such as tennis balls and the like.

There is a need for a ball tester which is of simple construction and easy to use and yet which will provide accurate readings every time a ball is tested. It is well-known that the internal pressure of a tennis ball is an important factor in determining the playing characteristics of the ball. Furthermore, the condition of the wall of the ball affects the playing characteristics of the ball, since the wall may lose its elasticity with use and may become harder as time goes by. The combination of the internal pressure of the ball plus the condition of the wall determines the playing characteristics of the ball. In the past, tennis players have tested tennis balls by manually squeezing it or bouncing it off of a surface. This gives a tennis player a general idea of the condition of the ball, but it is desirable to provide a more accurate means of determining the playing condition and pressure of the ball.

New tennis balls are manufactured with a fixed amount of internal pressure. This pressure diminishes with age and the amount of time the ball has been in play. Accordingly, different balls may have many different internal pressures. A tennis player does not need new tennis balls to play a consistent game, but he does require three balls in play of approximately equal internal pressure and playing condition.

The device of the invention enables tennis players to locate three balls of approximately the same pressure and playing condition when selecting from numerous new and used tennis balls in his possession. The player can therefore play with three balls which have similar internal pressures and playing characteristics. As a result, it is not necessary to buy as many new balls as usual since old balls may be used with satisfactory results. Additionally, by a simple reading of a gauge, a player can readily determine when a ball should be discarded.

SUMMARY OF THE INVENTION

The invention employs a pair of arms which are pivotally interconnected with one another. Each of the arms has a hand grip portion so that the device can be held in one hand and the hand grip portions squeezed toward one another. Each arm also includes a clamping portion, the two clamping portions being movable toward and away from one another to clamp a ball therebetween. A pair of support members are carried by the clamping portions for supporting and centering a ball within the tester.

A pressure and playing condition gauge is supported by one of the arms, and a ball engaging plunger is operatively connected to the gauge. When a ball is clamped between the clamping portions of the arms, the plunger will be moved a particular distance in accordance with the internal pressure of the ball and the condition of the wall of the ball, and a visible reading is provided on the face of the pressure gauge so that a user can readily determine the internal pressure and playing condition of the ball.

The end surfaces of the ball clamping portions of the two arms are adapted to engage one another to limit movement of the ball clamping portions toward one another thereby providing a uniform clamping pressure on balls tested by the device so that accurate gauge readings are obtained at all times.

Resilient means is provided for normally urging the hand grip portions of the arms away from one another. In one form of the invention, the resilient means urges the clamping portions of the arms toward one another, while in a second form of the invention, the resilient means urges the clamping portions of the arms away from one another.

BRIEF DESCRIPTION OF THE DRAWINGS

FIG. 1 is a front elevation, partly in section, of one form of the invention;

FIG. 2 is a side view of the device shown in FIG. 1;

FIG. 3 is a front elevation showing the device in a different operative position;

FIG. 4 is a fragmentary view showing the position of the plunger of the device when engaging a new ball;

FIG. 5 is a view, partly in section, showing the position of the plunger when engaging an older ball having a low internal pressure;

FIG. 6 is a front elevation, partly in section, of a second form of the invention; and FIG. 7 is a side view of the device shown in FIG. 6.

DESCRIPTION OF THE PREFERRED EMBODIMENT

Referring now to the drawings wherein like reference characters designate corresponding parts throughout the several views, a first form of the invention is shown in FIGS. 1–3. The device is shown in clamping position in FIG. 1; and FIG. 3 shows the device in its open position for receiving a tennis ball.

A pair of arms 10 and 12 are provided, each of the arms being formed of a rigid material such as steel or a molded plastic substance. Arm 10 includes a hand grip portion 14 which joins with an integral ball clamping portion 16 having an end surface 18 formed thereon. Arm 12 includes a hand grip portion 20 which joins with an integral ball clamping portion 22 having an end surface 24 formed thereon. The hand grip portions of the device are movable toward and away from one another, and the clamping portions are movable toward and away from one another. The end surfaces 18 and 24 are adapted to engage each other to limit movement of the ball clamping portions 16 and 22 toward one another.

The arms are pivotally interconnected to one another by a rivet 26 which extends through suitable holes formed through ears 28 formed integral with arm 10 and a hole formed through arm 12. A conventional torsion spring 30 has opposite leg portions 32 and 34 which bear against the inner surfaces of arms 10 and 12 respectively with the intermediate portion of the spring being wrapped around rivet 26 so as to normally urge arms 10 and 12 away from one another into the clamping position shown in FIG. 1.

A pair of ball support members 40 and 42 are formed of a suitable material such as steel and are secured to the inner surfaces of clamping portions 16 and 22 of the two arms as by welding in such a manner that members 40 and 42 are adapted to engage diametrically opposite portions of a tennis ball 44 having a wall 46 as seen in FIG. 1. Members 40 and 42 have inwardly facing surfaces which form portions of a spherical surface which is complementary to the outer surface of the wall 46 of the tennis ball. The distance between the facing surfaces of members 40 and 42 when the device is in the clamping position shown in FIG. 1 should be substantially equal to the outer diameter of the ball being tested. Members 40 and 42 serve to support and center a ball within the tester when the internal pressure of a ball is being measured A pressure and playing condition measuring means is provided in the form of a conventional pressure gauge 50 supported on the outer surface of the clamping portion 22 of arm 12 in a suitable manner as by welding. It may also be supported by a bracket or may be suitably threaded onto a threaded part on the associated clamping portion. The gauge will measure a combination of internal pressure and the condition of the wall of the tennis ball which determine the playing characteristics of the ball. The gauge may typically measure pressures between one and thirteen pounds and provide a readout of the playing condition of the ball, indicating whether it be good, fair or should be discarded.

The gauge includes a spring-biased plunger 52 which serves as a ball engaging means as seen in FIG. 1. Plunger 52 extends slidably through a suitable hole formed through member 42 and normally extends beyond the inner surface of member 42 as seen in FIG. 3. As seen in FIG. 2, the gauge includes a face 54 having suitable indicia thereon to indicate the condition of the ball. For example, numerals may be provided to indicate ball pressure in p.s.i. A hand 56 having an arrow head thereon will point to the indicia so that a pressure reading may be readily made.

When the hand grip portions 14 and 20 of the two arms 10 and 12 are squeezed together as seen in FIG. 3, the clamping portions 16 and 22 are moved away from one another to receive a ball. After a ball is inserted between the clamping portions and into engagement with members 40 and 42, the pressure on the hand grip portions may be released, whereupon the resilient spring 30 urges the clamping portions together into the position shown in FIG. 1 where the ball has been centered by members 40 and 42. The plunger will be forced outwardly toward the gauge in accordance with the pressure of the ball, and a visual reading may be made on the face of the gauge to determine the internal pressure and playing condition of the ball. The hand grip portions may subsequently be squeezed together to release the ball, and the procedure for measuring internal pressure may be repeated with another ball.

Referring now to FIG. 4, the position of the plunger 52 of the gauge is shown when testing a new ball. It will be seen that the plunger 52 has been moved a maximum distance toward the gauge, thereby giving a maximum reading of the internal pressure and playing condition of the ball. Referring now to FIG. 5, a used ball with low internal pressure is shown, and it is seen that the plunger has not been moved any substantial distance toward the gauge, thereby giving a minimum reading of the internal pressure of the ball.

Referring now to FIGS. 6 and 7, a modified form of the invention is illustrated. A pair of arms 60 and 62 are provided and are formed of a suitable rigid material. Arm 60 includes a hand grip portion 64 which joins with an integral ball clamping portion 66 having an end surface 68 formed thereon. Arm 62 includes a hand grip portion 70 which joins with an integral ball clamping portion 72 having an end surface 74 formed thereon. The hand grip portions are movable toward and away from one another, and the clamping portions are movable toward and away from one another. The end surfaces 68 and 74 adapted to engage each other to limit movement of the ball clamping portions 66 and 72.

The arms are pivotally interconnected to one another by a rivet 76 which extends through suitable holes formed through arm 60 and spaced portions 78 and 80 of arm 62 as seen in FIG. 7. Arm 62 is provided with a cutout 82 between portions 78 and 80 for receiving an intermediate portion of arm 60. A conventional torsion spring 84 has opposite leg portions 86 and 88 which bear against the inner surfaces of arms 60 and 62 respectively, with the intermediate portion of the spring being wrapped around rivet 76 so as to normally urge arms 10 and 12 away from one another. The remaining components of the device shown in FIGS. 6 and 7 are of the same construction as those illustrated in FIGS. 1–3 and have been given the same reference numerals primed.

In the embodiment shown in FIGS. 6 and 7, the operation of the device is the opposite of the embodiment shown in FIGS. 1–3. As seen in FIG. 6, the second form of the invention is manually squeezed so as to urge the clamping portions 66 and 72 toward one another until surfaces 68 and 74 contact one another. The ball is thereby clamped between the clamping portions, and a reading of the pressure of the ball can be made by observing the position of the hand 56' with respect to the indicia on face 54' of the pressure gauge 50'. When manual pressure on the arms 60 and 62 is released, spring 84 will move the clamping portions 66 and 72 away from one another so that a tested ball can be removed and another ball inserted in operative position within the tester.

The invention has been described with reference to a preferred embodiment. Obviously, various modifications, alterations and other embodiments will occur to others upon reading and understanding this specification. It is our intention to include all such modifications, alterations and alternate embodiments insofar as they come within the scope of the appended claims or the equivalent thereof.

What is claimed is:

1. A ball pressure and playing condition tester comprising a pair of arms pivotally interconnected with one another, each of said arms including a hand grip portion and a ball clamping portion, said hand grip portions being movable toward and away from one another, said clamping portions being movable toward and away from one another, ball support members carried by each of said clamping positions at an intermediate portion thereof and having facing surfaces supporting and centering a ball within the tester, said clamping portions extending from said intermediate portions toward one another and terminating in end surfaces which are engageable with one another to positively limit movement of said clamping portions toward one another and to position said ball support members so that the distance between said facing surfaces is substantially equal to the outer diameter of a ball to be tested thereby ensuring uniform clamping pressure on a ball clamped between said clamping portions, and pressure measuring means supported by one of said arms and including ball engaging means for engaging a ball, said measuring means providing an indication of the pressure of a ball clamped between said ball support members.

2. A ball tester as defined in claim 1 wherein said facing surfaces of said ball support members form portions of a spherical surface complementary to the outer surface of a ball to be tested.

3. A ball tester as defined in claim 2 wherein said ball engaging engaging means comprises a plunger, one of said ball support members having a hole formed therethrough, said plunger extending slidably through said hole.

4. A ball tester as defined in claim 2 including resilient means normally urging said clamping portions of the arms toward one another.

5. A ball tester as defined in claim 2 including resilient means normally urging said clamping portions of the arms away from one another.

* * * * *